United States Patent
Lion et al.

(10) Patent No.: US 11,207,260 B2
(45) Date of Patent: *Dec. 28, 2021

(54) PHOSPHONIC ETHYLENIC POLYMER AND COSMETIC USES THEREOF

(71) Applicant: L'OREAL, Paris (FR)

(72) Inventors: Bertrand Lion, Aulnay-sous-Bois (FR); Laurent Sabatie, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 511 days.

This patent is subject to a terminal disclaimer.

(21) Appl. No.: 16/062,946

(22) PCT Filed: Dec. 16, 2016

(86) PCT No.: PCT/EP2016/081352
§ 371 (c)(1),
(2) Date: Jun. 15, 2018

(87) PCT Pub. No.: WO2017/108599
PCT Pub. Date: Jun. 29, 2017

(65) Prior Publication Data
US 2018/0360729 A1 Dec. 20, 2018

(30) Foreign Application Priority Data
Dec. 22, 2015 (FR) .................... 15 63115

(51) Int. Cl.
| | |
|---|---|
| *A61K 8/81* | (2006.01) |
| *A61Q 1/06* | (2006.01) |
| *A61K 8/58* | (2006.01) |
| *A61K 8/898* | (2006.01) |
| *A61K 8/19* | (2006.01) |
| *A61Q 1/04* | (2006.01) |
| *A61K 8/31* | (2006.01) |
| *A61K 8/25* | (2006.01) |
| *A61K 8/27* | (2006.01) |
| *A61K 8/29* | (2006.01) |
| *A61K 8/41* | (2006.01) |
| *C08F 220/18* | (2006.01) |

(52) U.S. Cl.
CPC .............. *A61K 8/8152* (2013.01); *A61K 8/19* (2013.01); *A61K 8/25* (2013.01); *A61K 8/27* (2013.01); *A61K 8/29* (2013.01); *A61K 8/31* (2013.01); *A61K 8/41* (2013.01); *A61K 8/585* (2013.01); *A61K 8/898* (2013.01); *A61Q 1/04* (2013.01); *A61Q 1/06* (2013.01); *A61K 2800/43* (2013.01); *A61K 2800/54* (2013.01); *A61K 2800/592* (2013.01); *A61K 2800/882* (2013.01); *A61K 2800/884* (2013.01); *C08F 220/1808* (2020.02)

(58) Field of Classification Search
CPC .......... A61K 8/8152; A61K 8/41; A61K 8/19; A61K 8/31; A61K 2800/54
See application file for complete search history.

(56) References Cited

U.S. PATENT DOCUMENTS

| | | | |
|---|---|---|---|
| 5,009,670 A * | 4/1991 | Martischius | .......... C10L 1/2468 44/385 |
| 6,114,426 A | 9/2000 | Burack et al. | |
| 8,420,174 B2 * | 4/2013 | Goethlich | ............ C09D 123/00 427/385.5 |
| 2011/0001775 A1 | 1/2011 | Nishiwaki et al. | |
| 2014/0199530 A1 * | 7/2014 | Katoh | .................. C09D 11/326 428/207 |
| 2014/0227210 A1 | 8/2014 | Farcet | |

FOREIGN PATENT DOCUMENTS

| | | |
|---|---|---|
| DE | 41 26 230 A1 | 2/1993 |
| WO | WO-2009/050122 A1 | 4/2009 |

* cited by examiner

*Primary Examiner* — Kortney L. Klinkel
(74) *Attorney, Agent, or Firm* — Polsinelli PC

(57) ABSTRACT

The invention relates to a cosmetic process for caring for or making up keratin materials, comprising the topical application to the keratin materials of a cosmetic composition comprising a phosphonic polymer derived from the polymerization of: (a) 45% to 95% by weight of ethylenic monomer bearing an at least $C_8$ linear or branched alkyl group; (b) 5% to 25% by weight of vinylphosphonic acid monomer; (c) 0 to 50% by weight of additional monomer chosen from linear or branched $C_1C_6$ alkyl (meth)acrylates, $C_6$-$C_{12}$ cycloalkyl (meth)acrylates, and polydimethylsiloxanes bearing a mono(meth)acryloyloxy end group, optionally combined with an additional compound chosen from polyamine compounds bearing several primary amine and/or secondary amine groups, aminosilanes, salts of divalent or trivalent metal ions, clays and metal oxides. The process makes it possible to obtain a film-forming deposit that has good resistance to water, to oil and to sebum. The film is also non-tacky and transfer-resistant. The invention also relates to polymers containing the three monomers (a), (b) and (c).

33 Claims, No Drawings

PHOSPHONIC ETHYLENIC POLYMER AND COSMETIC USES THEREOF

CROSS REFERENCE TO RELATED APPLICATIONS

This application is the National Phase of Application No. PCT/EP2016/081352 filed Dec. 16, 2016, which claims priority to Application No. 15 63115 filed in France on Dec. 22, 2015 under 35 U.S.C. § 119. The entire contents of each application are hereby incorporated by reference.

The present invention relates to a cosmetic process for treating keratin materials using an ethylenic polymer bearing a phosphonic acid group, and also to a kit for performing said process, and to certain novel polymers.

Cosmetic products often require the use of a film-forming polymer to obtain a deposit of the product on keratin materials that has good cosmetic properties. In particular, it is necessary for the film-forming deposit to have good persistence, in particular for the deposit not to transfer during contact with the fingers, clothing, a glass or a cup, and also good persistence on contact with water, especially rain or during showering or alternatively perspiration. Skin sebum may also damage the film-forming deposit.

It is known to those skilled in the art to use polymers in order to obtain these good persistence properties throughout the day. These polymers are of very different chemical nature and are generally conveyed either in a fatty phase or in an aqueous phase. Examples that may be mentioned include silicone resins, polyacrylates and latices.

Although these polymers do indeed afford persistence properties, in particular transfer resistance, they may have a certain level of discomfort: for example, after applying the product, they may have a tacky aspect.

There is thus still a need for polymers that can afford good persistence properties while at the same time maintaining a certain level of comfort during use.

The inventors have discovered that particular ethylenic polymers bearing a phosphonic acid group make it possible to obtain a film that has good flexibility to follow the deformations of the skin without becoming impaired.

This particular phosphonic polymer is readily conveyable in a hydrocarbon-based oil such as isododecane.

When this phosphonic polymer is combined with an additional compound chosen from amine compounds bearing several primary amine and/or secondary amine groups, amino alkoxysilanes, salts of divalent or trivalent metal ions, clays and metal oxides, it forms a film-forming deposit that has good water-resistance, oil-resistance (especially resistance to olive oil) and sebum-resistance properties. The film also has the property of not being tacky and of not transferring on contact with a finger. The deposit obtained thus has good persistence properties.

These good film-forming properties are also obtained when the polymer is combined with a non-volatile oil (often used in makeup products).

This phosphonic polymer combined with said additional compound forms a film-forming deposit that is suitable for making up the skin or the lips, such as foundations or lipsticks.

More precisely, one subject of the present invention is a process, especially a cosmetic process, for treating and especially for caring for or making up keratin materials, comprising the topical application to the keratin materials of a composition comprising a phosphonic polymer and optionally a physiologically acceptable medium, the phosphonic polymer being derived from the polymerization of:

(a) 25% to 95% by weight, relative to the total weight of monomers, of an ethylenic monomer bearing an at least $C_8$ linear or branched alkyl group;
(b) 5% to 25% by weight of vinylphosphonic acid monomer of formula (I) defined below;
(c) 0 to 50% by weight of additional monomer chosen from:
(i) linear or branched $C_1$-$C_6$ alkyl (meth)acrylate or $C_6$-$C_{12}$ cycloalkyl (meth)acrylate non-silicone monomers;
(ii) polydimethylsiloxane silicone monomers bearing a mono(meth)acryloyloxy end group as defined below;
the composition(s) used being anhydrous when the additional component is an amino alkoxysilane.

Such an ethylenic polymer is referred to hereinbelow as a phosphonic polymer.

A subject of the invention is also a composition comprising, in a physiologically acceptable medium, a phosphonic polymer as described previously.

A subject of the invention is in particular a process, especially a cosmetic process, for caring for or making up the skin or the lips, comprising the topical application to the skin or the lips of a composition, especially a cosmetic composition, comprising a phosphonic polymer as described previously.

According to one embodiment of the process according to the invention, the phosphonic polymer used consists of the monomers described hereinabove or hereinbelow, in the described contents.

According to a first embodiment of the process according to the invention, a composition derived from the mixing (extemporaneous) of a composition comprising a phosphonic polymer as described previously and an additional component as defined previously, or a composition containing same and comprising a physiologically acceptable medium, as defined previously, is applied topically to keratin materials, the composition derived from the mixing being anhydrous when the additional component is an amino alkoxysilane.

According to one embodiment of the process according to the invention, the mixing of the composition comprising the phosphonic polymer and of the additional component, or of the composition containing same, is performed in a time of between 1 minute and 24 hours before its application to keratin fibres, and preferably between 5 and 30 minutes.

According to a second embodiment of the process according to the invention, a composition comprising a phosphonic polymer as described previously and an additional component as defined below, or a composition containing same and comprising a physiologically acceptable medium, as defined below, are applied sequentially to keratin materials, the compositions used being anhydrous when the additional component is an amino alkoxysilane.

According to one embodiment of the process according to the invention, the composition comprising the phosphonic polymer is first applied to the keratin materials, and said additional component or a composition containing same and comprising a physiologically acceptable medium is then applied.

According to another embodiment, said additional component, or a composition containing same and comprising a physiologically acceptable medium, is applied first to the keratin materials, and the composition comprising the phosphonic polymer is then applied.

A subject of the invention is also a composition, especially a cosmetic composition, obtained by mixing a phosphonic polymer as described previously or a composition containing same and comprising a physiologically acceptable medium, and an additional component as defined below or a composition containing same and comprising a physiologically acceptable medium, the composition being anhydrous when the additional compound is an amino alkoxysilane.

A subject of the invention is also a kit comprising a first composition comprising said phosphonic polymer as described previously and a second composition comprising an additional component as defined below and comprising a physiologically acceptable medium, the first and second compositions each being packaged in a separate packaging assembly, the compositions being anhydrous when the additional compound is an amino alkoxysilane.

The composition packaging assembly is, in a known manner, any packaging that is suitable for storing cosmetic compositions (in particular a bottle, tube, spray bottle or aerosol bottle).

Such a kit allows the process for treating keratin materials according to the invention to be performed.

The process according to the invention is suitable for caring for or making up keratin materials, such as the skin, the lips or the nails.

A subject of the invention is also certain novel polymers.

The phosphonic polymer used according to the invention is an ethylenic polymer derived from the polymerization of:
(a) 45% to 95% by weight, relative to the total weight of monomers, of an ethylenic monomer bearing an at least $C_8$ linear or branched alkyl group;
(b) 5% to 25% by weight of vinylphosphonic acid monomer of formula (I) defined below;
(c) 0 to 50% by weight of additional monomer chosen from:
(i) linear or branched $C_1$-$C_6$ alkyl (meth)acrylate or $C_6$-$C_{12}$ cycloalkyl (meth)acrylate non-silicone monomers;
(ii) polydimethylsiloxane silicone monomers bearing a mono(meth)acryloyloxy end group as defined below;

The phosphonic polymer used according to the invention comprises an ethylenic monomer bearing an at least $C_8$ linear or branched alkyl group (referred to as a fatty-chain ethylenic monomer); said alkyl group may be a linear or branched $C_8$-$C_{22}$ or $C_8$ to $C_{12}$ alkyl group.

Such a fatty-chain ethylenic monomer may be chosen from:
a) linear or branched $C_8$-$C_{22}$ alkyl (meth)acrylates (i.e. comprising a $C_8$-$C_{22}$ alkyl group);
b) the (meth)acrylamides of formula $CH_2$=$C(R_1)$—$CONR_3R_4$ in which $R_1$ represents a hydrogen atom or a methyl radical, $R_3$ represents a hydrogen atom or a linear or branched $C_1$-$C_{12}$ alkyl group, and $R_4$ represents a linear or branched $C_8$ to $C_{12}$ alkyl group, such as an isooctyl, isononyl or undecyl group;
c) the vinyl esters of formula $R_5$—CO—O—CH=$CH_2$ in which $R_5$ represents a linear or branched $C_8$-$C_{22}$ alkyl group;
d) the ethers of formula $R_6$—O—CH=$CH_2$ in which $R_6$ represents a linear or branched $C_8$-$C_{22}$ alkyl group.

Linear or branched $C_8$-$C_{22}$ alkyl groups that may be mentioned include octyl, 2-ethylhexyl, isooctyl, nonyl, decyl, undecyl, lauryl, myristyl, palmityl, stearyl, eicosyl and behenyl, and especially a 2-ethylhexyl, lauryl, behenyl or stearyl group.

Preferably, the fatty-chain ethylenic monomer is chosen from linear or branched $C_8$-$C_{22}$ alkyl (meth)acrylates, for instance 2-ethylhexyl acrylate, 2-ethylhexyl methacrylate, lauryl acrylate, lauryl methacrylate, behenyl acrylate, behenyl methacrylate, stearyl acrylate and stearyl methacrylate.

2-Ethylhexyl acrylate, stearyl acrylate or stearyl methacrylate is preferably used.

2-Ethylhexyl acrylate is preferentially used.

The fatty-chain monomer may be present in said ethylenic polymer in a content ranging from 45% to 95% by weight and preferably ranging from 55% to 95% by weight, relative to the total weight of monomers.

In the absence of additional monomer in the ethylenic polymer, the fatty-chain monomer may be present in a content ranging from 75% to 95% by weight, preferably ranging from 85% to 95% by weight and preferentially ranging from 87% to 93% by weight, relative to the total weight of monomers.

In the presence of additional monomer in the phosphonic polymer, the fatty-chain monomer may be present in a content ranging from 45% to 94.5% by weight, preferably ranging from 45% to 90% by weight, preferentially ranging from 55% to 80% by weight and more preferentially ranging from 58% to 73% by weight, relative to the total weight of monomers.

The vinylphosphonic acid monomer corresponds to the following formula (I):

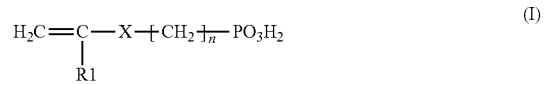

in which:
R1 denotes H or —$CH_3$;
X denotes a covalent bond and n denotes an integer ranging from 0 to 14;
or X denotes a —COO— group and n denotes an integer ranging from 2 to 6.

Advantageously, for the monomer of formula (I), X denotes a covalent bond and n is an integer ranging from 0 to 6 or X denotes a —COO— group and n is an integer ranging from 2 to 4.

Preferably, for the monomer of formula (I):

R1=H

X denotes a covalent bond and n denotes an integer ranging from 0 to 4.

As examples of monomers of formula (I), mention may be made of:
vinylphosphonic acid;
3-butenylphosphonic acid;
4-pentenylphosphonic acid;
10-undecenylphosphonic acid;
11-dodecenylphosphonic acid;
2-phosphonoethyl ester of 2-propenoic acid;
2-phosphonoethyl ester of 2-methyl-2-propenoic acid.

Preferably, monomer (I) is vinylphosphonic acid.

The vinylphosphonic acid monomer (I) may be present in said phosphonic polymer in a content ranging from 5% to 15% by weight and preferably ranging from 7% to 13% by weight, relative to the total weight of monomers.

The additional non-silicone monomer chosen from linear or branched $C_1$-$C_6$ alkyl (meth) acrylates may be, for example, methyl (meth)acrylate, ethyl (meth)acrylate, propyl (meth)acrylate, n-butyl (meth)acrylate, isobutyl (meth)acrylate, pentyl (meth)acrylate or hexyl (meth)acrylate.

The $C_6$-$C_{12}$ cycloalkyl (meth)acrylate is preferably isobornyl (meth)acrylate.

The additional non-silicone monomer may be present in said phosphonic polymer in a content ranging from 0.5% to 50% by weight, relative to the total weight of monomers, preferably ranging from 5% to 50% by weight, preferentially ranging from 15% to 40% by weight and more preferentially ranging from 20% to 35% by weight.

The additional silicone monomer is a polydimethylsiloxane bearing a mono(meth)acryloyloxy end group of formula (II) (referred to hereinbelow as a silicone monomer) below:

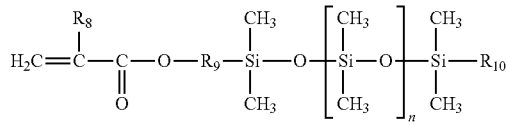

(II)

in which:

R$_8$ denotes a hydrogen atom or a methyl group; preferably methyl;

R$_9$ denotes a linear or branched, preferably linear, divalent hydrocarbon-based group containing from 1 to 10 carbon atoms, preferably containing from 2 to 4 carbon atoms, and optionally containing one or two —O— ether bonds; preferably an ethylene, propylene or butylene group;

R$_{10}$ denotes a linear or branched alkyl group containing from 1 to 10 carbon atoms, especially from 2 to 8 carbon atoms; preferably methyl, ethyl, propyl, butyl or pentyl;

n denotes an integer ranging from 1 to 300, preferably ranging from 3 to 200 and preferentially ranging from 5 to 100.

Use may be made in particular of monomethacryloyloxypropyl polydimethylsiloxanes such as those sold under the names MCR-M07, MCR-M17, MCR-M11 and MCR-M22 by Gelest Inc or the silicone macromonomers sold under the names X-22-2475, X-22-2426 and X-22-174DX by Shin-Etsu.

The additional silicone monomer (II) may be present in said phosphonic polymer in a content ranging from 5% to 50% by weight, relative to the total weight of monomers, preferably ranging from 15% to 40% by weight, preferentially ranging from 20% to 35% by weight and especially ranging from 25% to 35% by weight.

According to one embodiment of the invention, the phosphonic polymer does not comprise any additional monomer: it is formed from ethylenic monomer bearing an at least C$_8$ linear or branched alkyl group and maleic anhydride.

According to another embodiment of the invention, the phosphonic polymer comprises at least one additional monomer as defined previously. The additional monomer may be present in said phosphonic polymer in a content ranging from 5% to 50% by weight, relative to the total weight of monomers, preferably ranging from 15% to 40% by weight, preferentially ranging from 20% to 35% by weight and especially ranging from 25% to 35% by weight.

According to another embodiment of the invention, the phosphonic polymer comprises at least one additional non-silicone monomer as defined previously. Preferably, it is a C$_6$-C$_{12}$ cycloalkyl (meth)acrylate.

According to another embodiment of the invention, the phosphonic polymer comprises at least one additional silicone monomer as defined previously.

According to another embodiment of the invention, the phosphonic polymer comprises at least one additional non-silicone monomer and at least one additional silicone monomer as defined previously.

According to a first embodiment of the invention, the phosphonic polymer comprises, or consists of:

(a) 75% to 95% by weight, relative to the total weight of monomers, of linear or branched C$_8$-C$_{22}$ alkyl (meth)acrylate;

(b) 5% to 25% by weight of vinylphosphonic acid monomer of formula (I) as defined previously.

The phosphonic polymer especially comprises, or consists of:

(a) 75% to 95% by weight, relative to the total weight of monomers, of linear or branched C$_8$-C$_{18}$ alkyl (meth)acrylate;

(b) 5% to 25% by weight of vinylphosphonic acid monomer of formula (I) as defined previously.

In particular, the phosphonic polymer comprises, or consists of:

(a) 75% to 95% by weight, relative to the total weight of monomers, of 2-ethylhexyl (meth)acrylate;

(b) 5% to 25% by weight of vinylphosphonic acid.

In particular, the phosphonic polymer comprises, or consists of:

(a) 75% to 95% by weight, relative to the total weight of monomers, of stearyl (meth)acrylate;

(b) 5% to 25% by weight of vinylphosphonic acid.

In particular, the phosphonic polymer comprises, or consists of:

(a) 75% to 95% by weight, relative to the total weight of monomers, of a mixture of 2-ethylhexyl (meth)acrylate and of stearyl (meth)acrylate;

(b) 5% to 25% by weight of vinylphosphonic acid.

Preferably, the phosphonic polymer comprises, or consists of:

(a) 85% to 95% by weight, relative to the total weight of monomers, of linear or branched C$_8$-C$_{22}$ alkyl (meth)acrylate;

(b) 5% to 15% by weight of vinylphosphonic acid monomer of formula (I) as defined previously.

The phosphonic polymer especially comprises, or consists of:

(a) 85% to 95% by weight, relative to the total weight of monomers, of linear or branched C$_8$-C$_{18}$ alkyl (meth)acrylate;

(b) 5% to 15% by weight of vinylphosphonic acid monomer of formula (I) as defined previously.

In particular, the phosphonic polymer comprises, or consists of:

(a) 85% to 95% by weight, relative to the total weight of monomers, of 2-ethylhexyl (meth)acrylate;

(b) 5% to 15% by weight of vinylphosphonic acid.

In particular, the phosphonic polymer comprises, or consists of:

(a) 85% to 95% by weight, relative to the total weight of monomers, of stearyl (meth)acrylate;

(b) 5% to 15% by weight of vinylphosphonic acid.

In particular, the phosphonic polymer comprises, or consists of:

(a) 85% to 95% by weight, relative to the total weight of monomers, of a mixture of 2-ethylhexyl (meth)acrylate and of stearyl (meth)acrylate;

(b) 5% to 15% by weight of vinylphosphonic acid.

Preferentially, the phosphonic polymer comprises, or consists of:
(a) 87% to 93% by weight, relative to the total weight of monomers, of linear or branched $C_8$-$C_{22}$ alkyl (meth)acrylate;
(b) 7% to 13% by weight of vinylphosphonic acid monomer of formula (I) as defined previously.

The phosphonic polymer especially comprises, or consists of:
(a) 87% to 93% by weight, relative to the total weight of monomers, of linear or branched $C_8$-$C_{18}$ alkyl (meth)acrylate;
(b) 7% to 13% by weight of vinylphosphonic acid monomer of formula (I) as defined previously.

In particular, the phosphonic polymer comprises, or consists of:
(a) 87% to 93% by weight, relative to the total weight of monomers, of 2-ethylhexyl (meth)acrylate;
(b) 7% to 13% by weight of vinylphosphonic acid.

In particular, the phosphonic polymer comprises, or consists of:
(a) 87% to 93% by weight, relative to the total weight of monomers, of stearyl (meth)acrylate;
(b) 7% to 13% by weight of vinylphosphonic acid.

In particular, the phosphonic polymer comprises, or consists of:
(a) 87% to 93% by weight, relative to the total weight of monomers, of a mixture of 2-ethylhexyl (meth)acrylate and of stearyl (meth)acrylate;
(b) 7% to 13% by weight of vinylphosphonic acid.

The phosphonic polymer may be chosen from the following copolymers:
2-ethylhexyl acrylate/vinylphosphonic acid
stearyl acrylate/vinylphosphonic acid
2-ethylhexyl acrylate/stearyl acrylate/vinylphosphonic acid
in the respective monomer contents described previously, and in particular:
the 2-ethylhexyl acrylate/vinylphosphonic acid copolymer (90/10 mass composition).

According to a second embodiment of the invention, the phosphonic polymer comprises, or consists of:
(a) 45% to 94.5% by weight, relative to the total weight of monomers, of linear or branched $C_8$-$C_{22}$ alkyl (meth)acrylate;
(b) 5% to 25% by weight of vinylphosphonic acid monomer of formula (I) as defined previously;
(c) 0.5% to 50% by weight of additional non-silicone monomer chosen from linear or branched $C_1$-$C_6$ alkyl (meth)acrylates or $C_6$-$C_{12}$ cycloalkyl (meth)acrylates.

The phosphonic polymer especially comprises, or consists of:
(a) 45% to 94.5% by weight, relative to the total weight of monomers, of linear or branched $C_8$-$C_{18}$ alkyl (meth)acrylate;
(b) 5% to 25% by weight of vinylphosphonic acid monomer of formula (I) as defined previously;
(c) 0.5% to 50% by weight of $C_6$-$C_{12}$ cycloalkyl (meth)acrylate.

In particular, the phosphonic polymer comprises, or consists of:
(a) 45% to 94.5% by weight, relative to the total weight of monomers, of 2-ethylhexyl (meth)acrylate;
(b) 5% to 25% by weight of vinylphosphonic acid;
(c) 0.5% to 50% by weight of isobornyl (meth)acrylate.

In particular, the phosphonic polymer comprises, or consists of:
(a) 45% to 94.5% by weight, relative to the total weight of monomers, of stearyl (meth)acrylate;
(b) 5% to 25% by weight of vinylphosphonic acid;
(c) 0.5% to 50% by weight of isobornyl (meth)acrylate.

In particular, the phosphonic polymer comprises, or consists of:
(a) 45% to 94.5% by weight, relative to the total weight of monomers, of a mixture of 2-ethylhexyl (meth)acrylate and of stearyl (meth)acrylate;
(b) 5% to 25% by weight of vinylphosphonic acid;
(c) 0.5% to 50% by weight of isobornyl (meth)acrylate.

Preferably, the phosphonic polymer comprises, or consists of:
(a) 45% to 90% by weight, relative to the total weight of monomers, of linear or branched $C_8$-$C_{22}$ alkyl (meth)acrylate;
(b) 5% to 25% by weight of vinylphosphonic acid monomer of formula (I) as defined previously;
(c) 5% to 50% by weight of additional non-silicone monomer chosen from linear or branched $C_1$-$C_6$ alkyl (meth)acrylates or $C_6$-$C_{12}$ cycloalkyl (meth)acrylates.

The phosphonic polymer especially comprises, or consists of:
(a) 45% to 90% by weight, relative to the total weight of monomers, of linear or branched $C_8$-$C_{18}$ alkyl (meth)acrylate;
(b) 5% to 25% by weight of vinylphosphonic acid monomer of formula (I) as defined previously;
(c) 5% to 50% by weight of $C_6$-$C_{12}$ cycloalkyl (meth)acrylate.

In particular, the phosphonic polymer comprises, or consists of:
(a) 45% to 90% by weight, relative to the total weight of monomers, of 2-ethylhexyl (meth)acrylate;
(b) 5% to 25% by weight of vinylphosphonic acid;
(c) 5% to 50% by weight of isobornyl (meth)acrylate.

In particular, the phosphonic polymer comprises, or consists of:
(a) 45% to 90% by weight, relative to the total weight of monomers, of stearyl (meth)acrylate;
(b) 5% to 25% by weight of vinylphosphonic acid;
(c) 5% to 50% by weight of isobornyl (meth)acrylate.

In particular, the phosphonic polymer comprises, or consists of:
(a) 45% to 90% by weight, relative to the total weight of monomers, of a mixture of 2-ethylhexyl (meth)acrylate and of stearyl (meth)acrylate;
(b) 5% to 25% by weight of vinylphosphonic acid;
(c) 5% to 50% by weight of isobornyl (meth)acrylate.

Preferentially, the phosphonic polymer comprises, or consists of:
(a) 55% to 80% by weight, relative to the total weight of monomers, of linear or branched $C_8$-$C_{22}$ alkyl (meth)acrylate;
(b) 5% to 15% by weight of vinylphosphonic acid monomer of formula (I) as defined previously;
(c) 15% to 40% by weight of additional non-silicone monomer chosen from linear or branched $C_1$-$C_6$ alkyl (meth)acrylates or $C_6$-$C_{12}$ cycloalkyl (meth)acrylates.

The phosphonic polymer especially comprises, or consists of:
(a) 55% to 80% by weight, relative to the total weight of monomers, of linear or branched $C_8$-$C_{18}$ alkyl (meth)acrylate;

(b) 5% to 15% by weight of vinylphosphonic acid monomer of formula (I) as defined previously;
(c) 15% to 40% by weight of $C_6$-$C_{12}$ cycloalkyl (meth)acrylate.

In particular, the phosphonic polymer comprises, or consists of:
(a) 55% to 80% by weight, relative to the total weight of monomers, of 2-ethylhexyl (meth)acrylate;
(b) 5% to 15% by weight of vinylphosphonic acid;
(c) 15% to 40% by weight of isobornyl (meth)acrylate.

In particular, the phosphonic polymer comprises, or consists of:
(a) 55% to 80% by weight, relative to the total weight of monomers, of stearyl (meth)acrylate;
(b) 5% to 15% by weight of vinylphosphonic acid;
(c) 15% to 40% by weight of isobornyl (meth)acrylate.

In particular, the phosphonic polymer comprises, or consists of:
(a) 55% to 80% by weight, relative to the total weight of monomers, of a mixture of 2-ethylhexyl (meth)acrylate and of stearyl (meth)acrylate;
(b) 5% to 15% by weight of vinylphosphonic acid;
(c) 15% to 40% by weight of isobornyl (meth)acrylate.

More preferentially, the phosphonic polymer comprises, or consists of:
(a) 58% to 73% by weight, relative to the total weight of monomers, of linear or branched $C_8$-$C_{22}$ alkyl (meth)acrylate;
(b) 7% to 13% by weight of vinylphosphonic acid monomer of formula (I) as defined previously;
(c) 20% to 35% by weight of additional non-silicone monomer chosen from linear or branched $C_1$-$C_6$ alkyl (meth)acrylates or $C_6$-$C_{12}$ cycloalkyl (meth)acrylates.

The phosphonic polymer especially comprises, or consists of:
(a) 58% to 73% by weight, relative to the total weight of monomers, of linear or branched $C_8$-$C_{18}$ alkyl (meth)acrylate;
(b) 7% to 13% by weight of vinylphosphonic acid monomer of formula (I) as defined previously;
(c) 20% to 35% by weight of $C_6$-$C_{12}$ cycloalkyl (meth)acrylate.

In particular, the phosphonic polymer comprises, or consists of:
(a) 58% to 73% by weight, relative to the total weight of monomers, of 2-ethylhexyl (meth)acrylate;
(b) 7% to 13% by weight of vinylphosphonic acid;
(c) 20% to 35% by weight of isobornyl (meth)acrylate.

In particular, the phosphonic polymer comprises, or consists of:
(a) 58% to 73% by weight, relative to the total weight of monomers, of stearyl (meth)acrylate;
(b) 7% to 13% by weight of vinylphosphonic acid;
(c) 20% to 35% by weight of isobornyl (meth)acrylate.

In particular, the phosphonic polymer comprises, or consists of:
(a) 58% to 73% by weight, relative to the total weight of monomers, of a mixture of 2-ethylhexyl (meth)acrylate and of stearyl (meth)acrylate;
(b) 7% to 13% by weight of vinylphosphonic acid;
(c) 20% to 35% by weight of isobornyl (meth)acrylate.

The phosphonic polymer may be chosen from the following copolymers:
2-ethylhexyl acrylate/vinylphosphonic acid/isobornyl (meth)acrylate
stearyl acrylate/vinylphosphonic acid/isobornyl (meth)acrylate
2-ethylhexyl acrylate/stearyl acrylate/vinylphosphonic acid/isobornyl (meth)acrylate
in the respective monomer contents described previously; and in particular:
the 2-ethylhexyl acrylate/isobornyl acrylate/vinylphosphonic acid copolymer (70/20/10 mass composition).

According to a third embodiment of the invention, the phosphonic polymer comprises, or consists of:
(a) 45% to 94.5% by weight, relative to the total weight of monomers, of linear or branched $C_8$-$C_{22}$ alkyl (meth)acrylate;
(b) 5% to 25% by weight of vinylphosphonic acid monomer of formula (I) as defined previously;
(c) 0.5% to 50% by weight of silicone monomer (II) as described previously.

The phosphonic polymer especially comprises, or consists of:
(a) 45% to 94.5% by weight, relative to the total weight of monomers, of linear or branched $C_8$-$C_{18}$ alkyl (meth)acrylate;
(b) 5% to 25% by weight of vinylphosphonic acid monomer of formula (I) as defined previously;
(c) 0.5% to 50% by weight of silicone monomer (II) as described previously.

In particular, the phosphonic polymer comprises, or consists of:
(a) 45% to 94.5% by weight, relative to the total weight of monomers, of 2-ethylhexyl (meth)acrylate;
(b) 5% to 25% by weight of vinylphosphonic acid;
(c) 0.5% to 50% by weight of silicone monomer (II) as described previously.

In particular, the phosphonic polymer comprises, or consists of:
(a) 45% to 94.5% by weight, relative to the total weight of monomers, of sterile (meth)acrylate;
(b) 5% to 25% by weight of vinylphosphonic acid;
(c) 0.5% to 50% by weight of silicone monomer (II) as described previously.

In particular, the phosphonic polymer comprises, or consists of:
(a) 45% to 94.5% by weight, relative to the total weight of monomers, of a mixture of 2-ethylhexyl (meth)acrylate and of stearyl (meth)acrylate;
(b) 5% to 25% by weight of vinylphosphonic acid;
(c) 0.5% to 50% by weight of silicone monomer (II) as described previously.

Preferably, the phosphonic polymer comprises, or consists of:
(a) 45% to 90% by weight, relative to the total weight of monomers, of linear or branched $C_8$-$C_{22}$ alkyl (meth)acrylate;
(b) 5% to 25% by weight of vinylphosphonic acid monomer of formula (I) as defined previously;
(c) 5% to 50% by weight of silicone monomer (II) as described previously.

The phosphonic polymer especially comprises, or consists of:
(a) 45% to 90% by weight, relative to the total weight of monomers, of linear or branched $C_8$-$C_{18}$ alkyl (meth)acrylate;
(b) 5% to 25% by weight of vinylphosphonic acid monomer of formula (I) as defined previously;
(c) 5% to 50% by weight of silicone monomer (II) as described previously.

In particular, the phosphonic polymer comprises, or consists of:
(a) 45% to 90% by weight, relative to the total weight of monomers, of 2-ethylhexyl (meth)acrylate;
(b) 5% to 25% by weight of vinylphosphonic acid;
(c) 5% to 50% by weight of silicone monomer (II) as described previously.

In particular, the phosphonic polymer comprises, or consists of:
(a) 45% to 90% by weight, relative to the total weight of monomers, of stearyl (meth)acrylate;
(b) 5% to 25% by weight of vinylphosphonic acid;
(c) 5% to 50% by weight of silicone monomer (II) as described previously.

In particular, the phosphonic polymer comprises, or consists of:
(a) 45% to 90% by weight, relative to the total weight of monomers, of a mixture of 2-ethylhexyl (meth)acrylate and of stearyl (meth)acrylate;
(b) 5% to 25% by weight of vinylphosphonic acid;
(c) 5% to 50% by weight of silicone monomer (II) as described previously.

Preferentially, the phosphonic polymer comprises, or consists of:
(a) 55% to 80% by weight, relative to the total weight of monomers, of linear or branched $C_8$-$C_{22}$ alkyl (meth)acrylate;
(b) 5% to 15% by weight of vinylphosphonic acid monomer of formula (I) as defined previously;
(c) 15% to 40% by weight of silicone monomer (II) as described previously.

The phosphonic polymer especially comprises, or consists of:
(a) 55% to 80% by weight, relative to the total weight of monomers, of linear or branched $C_8$-$C_{18}$ alkyl (meth)acrylate;
(b) 5% to 15% by weight of vinylphosphonic acid monomer of formula (I) as defined previously;
(c) 15% to 40% by weight of silicone monomer (II) as described previously.

In particular, the phosphonic polymer comprises, or consists of:
(a) 55% to 80% by weight, relative to the total weight of monomers, of 2-ethylhexyl (meth)acrylate;
(b) 5% to 15% by weight of vinylphosphonic acid;
(c) 15% to 40% by weight of silicone monomer (II) as described previously.

In particular, the phosphonic polymer comprises, or consists of:
(a) 55% to 80% by weight, relative to the total weight of monomers, of stearyl (meth)acrylate;
(b) 5% to 15% by weight of vinylphosphonic acid;
(c) 15% to 40% by weight of silicone monomer (II) as described previously.

In particular, the phosphonic polymer comprises, or consists of:
(a) 55% to 80% by weight, relative to the total weight of monomers, of a mixture of 2-ethylhexyl (meth)acrylate and of stearyl (meth)acrylate;
(b) 5% to 15% by weight of vinylphosphonic acid;
(c) 15% to 40% by weight of silicone monomer (II) as described previously.

More preferentially, the phosphonic polymer comprises, or consists of:
(a) 58% to 73% by weight, relative to the total weight of monomers, of linear or branched $C_8$-$C_{22}$ alkyl (meth)acrylate;
(b) 7% to 13% by weight of vinylphosphonic acid monomer of formula (I) as defined previously;
(c) 20% to 35% by weight of silicone monomer (II) as described previously.

The phosphonic polymer especially comprises, or consists of:
(a) 58% to 73% by weight, relative to the total weight of monomers, of linear or branched $C_8$-$C_{18}$ alkyl (meth)acrylate;
(b) 7% to 13% by weight of vinylphosphonic acid monomer of formula (I) as defined previously;
(c) 20% to 35% by weight of silicone monomer (II) as described previously.

In particular, the phosphonic polymer comprises, or consists of:
(a) 58% to 73% by weight, relative to the total weight of monomers, of 2-ethylhexyl (meth)acrylate;
(b) 7% to 13% by weight of vinylphosphonic acid;
(c) 15% to 40% by weight of silicone monomer (II) as described previously.

In particular, the phosphonic polymer comprises, or consists of:
(a) 58% to 73% by weight, relative to the total weight of monomers, of stearyl (meth)acrylate;
(b) 7% to 13% by weight of vinylphosphonic acid;
(c) 15% to 40% by weight of silicone monomer (II) as described previously.

In particular, the phosphonic polymer comprises, or consists of:
(a) 58% to 73% by weight, relative to the total weight of monomers, of a mixture of 2-ethylhexyl (meth)acrylate and of stearyl (meth)acrylate;
(b) 7% to 13% by weight of vinylphosphonic acid;
(c) 15% to 40% by weight of silicone monomer (II) as described previously.

The ethylenic polymer may be chosen from the following copolymers:
2-ethylhexyl acrylate/vinylphosphonic acid/silicone monomer (II)
stearyl acrylate/vinylphosphonic acid/silicone monomer (II)
2-ethylhexyl acrylate/stearyl acrylate/vinylphosphonic acid/silicone monomer (II)
in the respective monomer contents described previously.

Advantageously, the phosphonic polymer has a weight-average molecular weight ranging from 5000 to 1 000 000 g/mol, preferably ranging from 10 000 to 500 000 g/mol and preferentially ranging from 15 000 to 350 000 g/mol.

Polymers containing monomers (a) and (b) described previously are known.

Patent application US-A-2014/0 199 530 describes $C_{12}$-$C_{22}$ alkyl (meth)acrylate/vinylphosphonic acid copolymers with a phosphonic monomer/(meth)acrylate monomer weight ratio ranging from 0.1 to 10 as dispersants for printing inks.

U.S. Pat. No. 8,420,174 describes in Examples 13 and 14 terpolymers of acrylic acid/vinylphosphonic acid/lauryl acrylate with respective monomer mass ratios of 35/15/50 and 52.5/22.5/25 used for coating metal surfaces.

U.S. Pat. No. 5,009,670 describes in Example 10 a stearyl acrylate/vinylphosphonic acid copolymer in a 70/30 mass ratio used as fuel additive.

Patent application DE 4126230 describes in Example 2 a vinylphosphonic acid/2-ethylhexyl acrylate/butyl acrylate/acrylic acid/methacrylic acid polymer in a 5/60/10/5/20 mass ratio as an adhesive.

A subject of the invention is thus also the novel polymers derived from the polymerization of:
(a) 75% to 95% by weight, relative to the total weight of monomers, of linear or branched $C_8$ alkyl (meth)acrylate;
(b) 5% to 25% by weight of vinylphosphonic acid monomer of formula (I) as defined previously.

A subject of the invention is also the novel polymers derived from the polymerization of:
(a) 45% to 94.5% by weight, relative to the total weight of monomers, of linear or branched $C_8$-$C_{22}$ alkyl (meth)acrylate;
(b) 5% to 25% by weight of vinylphosphonic acid monomer of formula (I) as defined previously;
(c) 0.5% to 50% by weight of additional monomer chosen from:
(i) $C_6$-$C_{12}$ cycloalkyl (meth)acrylates;
(ii) polydimethylsiloxane silicone monomers bearing a mono(meth)acryloyloxy end group as defined previously;
and also similar polymers with the contents described previously.

A subject of the invention is also the novel polymers derived from the polymerization of:
(a) 55% to 80% by weight, relative to the total weight of monomers, of linear or branched $C_8$-$C_{22}$ alkyl (meth)acrylate;
(b) 5% to 15% by weight of vinylphosphonic acid monomer of formula (I) as defined previously;
(c) 15% to 40% by weight of additional monomer chosen from linear or branched $C_1$-$C_6$ alkyl (meth)acrylate non-silicone monomers.

A subject of the invention is also the novel polymers described previously as second and third embodiments.

A subject of the invention is also the novel polymers derived from the polymerization of:
(a) 45% to 95% by weight, relative to the total weight of monomers, of an ethylenic monomer bearing an at least $C_8$ linear or branched alkyl group chosen from:
i) the (meth)acrylamides of formula $CH_2=C(R_1)$—$CONR_3R_4$ in which $R_1$ represents a hydrogen atom or a methyl radical, $R_3$ represents a hydrogen atom or a linear or branched $C_1$-$C_{12}$ alkyl group, and $R_4$ represents a linear or branched $C_8$ to $C_{12}$ alkyl group, such as an isooctyl, isononyl or undecyl group.
ii) the vinyl esters of formula $R_5$—CO—O—CH=$CH_2$ in which $R_5$ represents a linear or branched $C_8$-$C_{22}$ alkyl group;
iii) the ethers of formula $R_6$—O—CH=$CH_2$ in which $R_6$ represents a linear or branched $C_8$-$C_{22}$ alkyl group;
(b) 5% to 25% by weight of vinylphosphonic acid monomer of formula (I) defined below;
(c) 0% to 50% by weight of additional monomer chosen from:
(i) linear or branched $C_1$-$C_6$ alkyl (meth)acrylate or $C_6$-$C_{12}$ cycloalkyl (meth)acrylate non-silicone monomers;
(ii) polydimethylsiloxane silicone monomers bearing a mono(meth)acryloyloxy end group as defined previously;
and also similar polymers with the following preferred contents:
a) 75% to 95% and (b) 5% to 25%; (a) 85% to 95% and (b) 5% to 15%; (a) 87% to 93% and (b) 7% to 13%;
(a) 45% to 94.5% and (b) 5% to 25% and (c) 0.5% to 50%;
(a) 45% to 90% and (b) 5% to 25% and (c) 5% to 50%; (a) 55% to 80% and (b) 5% to 15% and (c) 15% to 40%; (a) 58% to 73% and (b) 7% to 13% and (c) 20% to 35%.

The invention also relates to a composition comprising, in a physiologically acceptable medium, a novel polymer as described previously.

The polymer used according to the invention may be used in a composition comprising a physiologically acceptable medium, in particular in a cosmetic composition.

The term "physiologically acceptable medium" means a medium that is compatible with human keratin materials, in particular with the skin and the lips.

The term "cosmetic composition" is understood to mean a composition that is compatible with keratin materials, which has a pleasant colour, odour and feel and which does not cause unacceptable discomfort (stinging, tautness or redness) liable to discourage the consumer from using it.

The phosphonic polymer as defined previously may be present in the composition used according to the invention in a content ranging from 0.1% to 40% by weight, relative to the total weight of the composition, preferably from 0.5% to 35% by weight of active material, preferentially ranging from 1% to 30% by weight, and more preferentially ranging from 10% to 30% by weight.

The additional component used in the process according to the invention is especially an amine compound chosen from polyamine compounds containing one or more primary amine and/or secondary amine groups or alternatively amino alkoxysilanes. It may thus be chosen from amino alkoxysilanes, diamine compounds and triamine compounds.

According to a first embodiment of the invention, the polyamine compound is a compound comprising from 2 to 20 carbon atoms, in particular a non-polymeric compound. The term "non-polymeric compound" means a compound which is not directly obtained via a monomer polymerization reaction.

Polyamine compounds that may be mentioned include N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine, 1,3-propylenediamine, 1,4-butylenediamine, lysine, cystamine, xylenediamine, tris(2-aminoethyl)amine and spermidine. Preferably, the amine compound is chosen from ethylenediamine, 1,3-propylenediamine and 1,4-butylenediamine. Preferentially, the polyamine compound is ethylenediamine.

The amine compound may also be chosen from amino alkoxysilanes, such as those of formula (III):

$$R'_1Si(OR'_2)_z(R'_3)_x \quad (III)$$

in which:
R'$_1$ is a linear or branched, saturated or unsaturated, cyclic or acyclic $C_1$-$C_6$ hydrocarbon-based chain substituted with a group chosen from the following groups:
amine $NH_2$ or NHR with R=$C_1$-$C_4$ alkyl,
an aryl or aryloxy group substituted with an amino group or with a $C_1$-$C_4$ aminoalkyl group,
R'$_1$ possibly being interrupted in its chain with a heteroatom (O, S, NH) or a carbonyl group (CO), R'$_1$ being linked to the silicon atom directly via a carbon atom,
R'$_2$ and R'$_3$, which may be identical or different, represent a linear or branched alkyl group comprising from 1 to 6 carbon atoms,
z denotes an integer ranging from 1 to 3, and
x denotes an integer ranging from 0 to 2,
with z+x=3.

Preferably, R'$_2$ represents an alkyl group comprising from 1 to 4 carbon atoms.

Preferably, $R'_2$ represents a linear alkyl group, comprising from 1 to 4 carbon atoms.

Preferably, $R'_2$ represents an ethyl group.

Preferably, $R'_3$ represents an alkyl group comprising from 1 to 4 carbon atoms.

Preferably, $R'_3$ represents a linear alkyl group, comprising from 1 to 4 carbon atoms.

Preferably, $R'_3$ represents a methyl or ethyl group.

Preferably, $R'_1$ is an acyclic chain.

Preferably, $R'_1$ is a linear or branched, saturated or unsaturated $C_1$-$C_6$ hydrocarbon-based chain, substituted with an amine group $NH_2$ or NHR (R=$C_1$-$C_6$ alkyl, $C_3$-$C_6$ cycloalkyl or $C_6$ aromatic). Preferentially, $R'_1$ is a saturated linear $C_1$-$C_6$ hydrocarbon-based chain substituted with an amine group $NH_2$. More preferentially, $R'_1$ is a saturated linear $C_2$-$C_4$ hydrocarbon-based chain substituted with an amine group $NH_2$.

Preferably, $R'_1$ is a saturated linear $C_1$-$C_6$ hydrocarbon-based chain substituted with an amine group $NH_2$, $R'_2$ represents an alkyl group comprising from 1 to 4 carbon atoms, $R'_3$ represents an alkyl group comprising from 1 to 4 carbon atoms.

Preferably, z is equal to 3.

Preferably, the aminosilane of formula (III) is chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane and N-(2-aminoethylaminomethyl) phenethyltrimethoxysilane.

Preferably, the aminosilane (III) is chosen from 3-aminopropyltriethoxysilane (APTES), 3-aminoethyltriethoxysilane (AETES), 3-aminopropylmethyldiethoxysilane and N-(2-aminoethyl)-3-aminopropyltriethoxysilane.

Preferably, the aminosilane (III) is 3-aminopropyltriethoxysilane (APTES).

Preferably, the amine compound is chosen from 3-aminopropyltriethoxysilane (APTES), N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine and lysine.

The polyamine compound may also be chosen from amine-based polymers, especially having a weight-average molecular weight ranging from 500 to 1 000 000, preferably ranging from 500 to 500 000, and preferentially ranging from 500 to 100 000.

As amine-based polymer, use may be made of poly(($C_2$-$C_5$)alkyleneimines), and in particular polyethyleneimines and polypropyleneimines, especially poly(ethyleneimine)s (for example the product sold under the reference 46,852-3 by the company Aldrich Chemical); poly(allylamine) (for example the product sold under the reference 47,913-6 by the company Aldrich Chemical); polyvinylamines and copolymers thereof, in particular with vinylamides; mention may in particular be made of vinylamine/vinylformamide copolymers such as those sold under the name Lupamin® 9030 by the company BASF; polyamino acids bearing $NH_2$ groups, such as polylysine, for example the product sold by the company JNC Corporation (formerly Chisso); aminodextran, such as the product sold by the company CarboMer Inc; amino polyvinyl alcohol, such as the product sold by the company CarboMer Inc, acrylamidopropylamine-based copolymers; chitosans; polydimethylsiloxanes comprising primary amine groups at the chain end or on side chains, for example aminopropyl side or end groups, for instance those of formula (A) or (B) or (C):

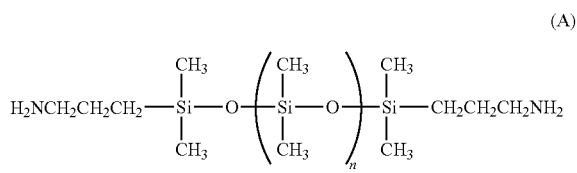

(A)

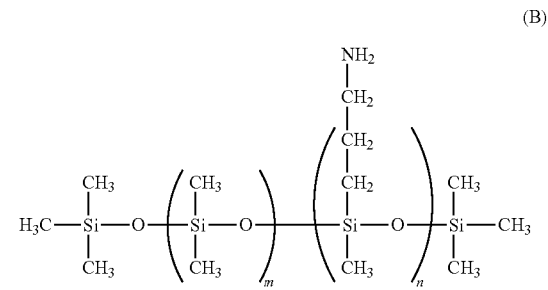

(B)

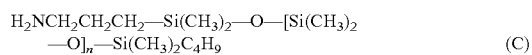

(C)

in formula (A): the value of n is such that the weight-average molecular weight of the silicone is between 500 and 55 000. As examples of aminosilicone (A), mention may be made of those sold under the names DMS-A11, DMS-A12, DMS-A15, DMS-A21, DMS-A31, DMS-A32 and DMS-A35 by the company Gelest, reference 481688 from Aldrich, in formula (B), the values of n and m are such that the weight-average molecular weight of the silicone is between 1000 and 55 000. As examples of silicone (B), mention may be made of those sold under the names AMS-132, AMS-152, AMS-162, AMS-163, AMS-191 and AMS-1203 by the company Gelest, in formula (C), the value of n is such that the weight-average molecular weight of the silicone is between 500 and 3000. As an example of silicone (C), mention may be made of those sold under the names MCR-A11 and MCR-A12 by the company Gelest;

amodimethicones of formula (D):

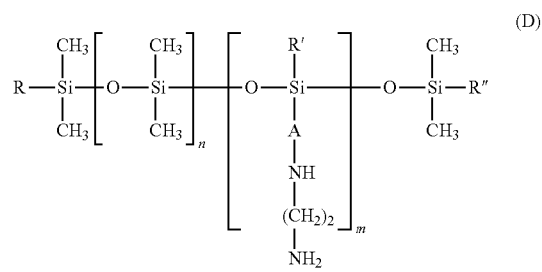

(D)

in which R, R' and R", which may be identical or different, each represent a $C_1$-$C_4$ alkyl or hydroxyl group, A represents a $C_3$ alkylene group and m and n are such that the weight-average molecular mass of the compound is between 5000 and 500 000 approximately;

the amodimethicones of formula (K):

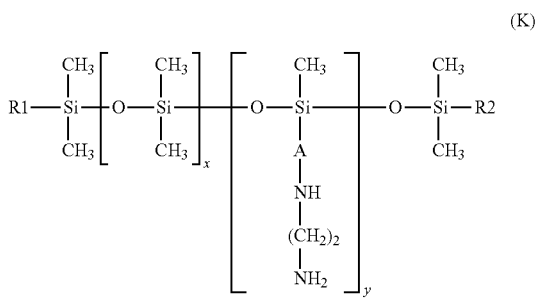

in which:
- R1 and R2, which may be identical or different, represent a linear or branched, saturated or unsaturated alkyl group comprising from 6 to 30 carbon atoms, preferably from 8 to 24 carbon atoms and preferentially from 12 to 20 carbon atoms,
- A represents a linear or branched alkylene group containing from 2 to 8 carbon atoms,
- x and y are integers ranging from 1 to 5000; preferably, x ranges from 10 to 2000 and especially from 100 to 1000; preferably, y ranges from 1 to 100.

Preferably, A comprises from 3 to 6 carbon atoms, in particular 4 carbon atoms; preferably, A is branched. A may be a divalent radical chosen from: —CH$_2$CH$_2$CH$_2$— and —CH$_2$CH(CH$_3$)CH$_2$—.

Preferably, R1 and R2, which may be identical or different, represent a saturated linear alkyl group comprising from 6 to 30 carbon atoms, preferentially from 8 to 24 carbon atoms and especially from 12 to 20 carbon atoms, for instance a dodecyl, tetradecyl, pentadecyl, hexadecyl, heptadecyl, octadecyl, nonadecyl or eicosyl group. Advantageously, R1 and R2 represent a mixture of hexadecyl (cetyl) and octadecyl (stearyl) radicals (mixture also known as cetearyl).

Preferentially, for the amodimethicone of formula (K):
- x ranges from 10 to 2000 and especially from 100 to 1000;
- y ranges from 1 to 100;
- A comprises from 3 to 6 carbon atoms, and in particular 4 carbon atoms; preferably, A is branched; preferentially, A is chosen from the divalent radicals: —CH$_2$CH$_2$CH$_2$— and —CH$_2$CH(CH$_3$)CH$_2$—; and
- R1 and R2, which may be identical or different, represent a saturated linear radical comprising from 6 to 30 carbon atoms, preferably from 8 to 24 carbon atoms and especially from 12 to 20 carbon atoms, for instance a dodecyl, tetradecyl, pentadecyl, hexadecyl, heptadecyl, octadecyl, nonadecyl or eicosyl group. Advantageously, R1 and R2 represent a mixture of hexadecyl (cetyl) and octadecyl (stearyl) radicals (mixture also known as cetearyl).

As amodimethicone of formula (K), use may be made of bis-cetearyl amodimethicone (INCI name), especially the product sold under the name Silsoft® AX by the company Momentive Performance Materials.

The polyether amines known especially under the reference Jeffamine® from the company Huntsman; and especially:
Polyethylene glycol and/or polypropylene glycol α,ω-diamines (bearing an amine function at the end of the chain), which may comprise from 2 to 80 units derived from propylene oxide, or which may comprise from 2 to 50 units derived from ethylene oxide and from 1 to 10 units derived from propylene oxide, for instance the products sold under the names Jeffamine® D-230, D-400, D-2000, D-4000, ED-600, ED-9000, ED-2003.

Polytetrahydrofuran (or polytetramethylene glycol) α,ω-diamines,
polybutadiene α,ω-diamines;
Polyamidoamine (PANAM) dendrimers bearing amine end functions.

Poly(meth)acrylates or poly(meth)acrylamides bearing primary or secondary amine side functions, such as poly(3-aminopropyl)methacrylamide or poly(2-aminoethyl) methacrylate;

As amine-based polymer, use is preferably made of polydimethylsiloxanes comprising primary amine groups at the chain end or on side chains.

Preferentially, polydimethylsiloxanes comprising aminopropyl end groups at the chain end are used.

Advantageously, the polyamine compounds used in the process according to the invention are chosen from ethylenediamine and polydimethylsiloxanes comprising primary amine groups at the chain end or on side chains.

Preferentially, the amine compounds used in the process according to the invention are chosen from polydimethylsiloxanes comprising primary amine groups at the chain end or on side chains, 3-aminopropyltriethoxysilane (APTES). More preferentially, polydimethylsiloxanes comprising aminopropyl end groups at the chain end, 3-aminopropyltriethoxysilane (APTES), are used.

Advantageously, the amine compound used in the process according to the invention is used in a mole ratio of amine group of the amine compound/phosphonic acid group of the phosphonic polymer ranging from 0.01 to 10, preferably ranging from 0.1 to 5, preferentially ranging from 0.1 to 2 and more preferentially ranging from 0.1 to 1. On contact with the phosphonic polymer, the polyamine compound reacts with the phosphonic acid functions to form a crosslinked polymer, for example in the following manner:

Scheme I

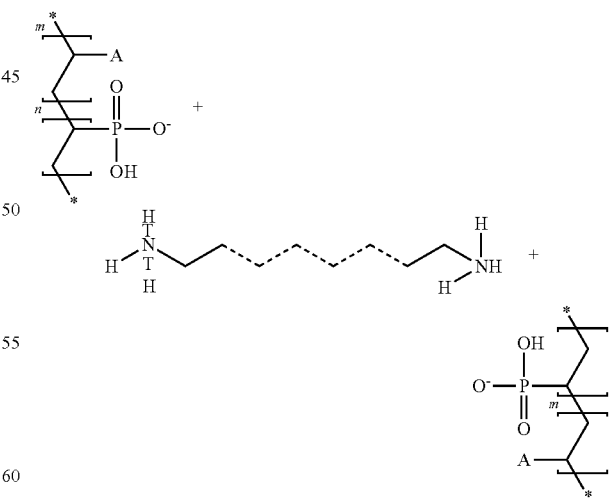

Such a crosslinked polymer is novel and thus also forms the subject of the present invention.

The crosslinked polymer may thus be obtained by reacting said polyamine compound with the phosphonic polymer described previously. Some or all of the anhydride groups react with the NH or NH$_2$ group of the polyamine compound and form a unit bearing an amide group and a carboxylic acid group as described in scheme I.

On contact with the phosphonic polymer, in anhydrous medium, the amino alkoxysilane compound (III) reacts with the phosphonic acid functions to form a unit having the following formula:

Scheme II

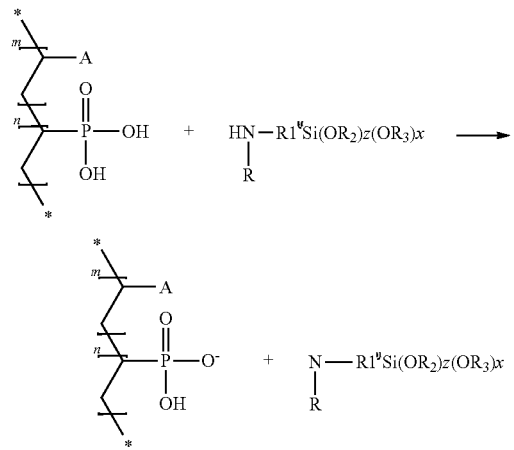

the unit bearing the group A symbolizing the unit derived from the fatty-chain ethylenic monomer.

Such a phosphonic polymer bearing an amino alkoxysilane group obtained by reacting the phosphonic polymer with the amino alkoxysilane compound (III) is novel and thus also forms the subject of the present invention. A subject of the invention is also an anhydrous composition comprising such a phosphonic polymer bearing an amino alkoxysilane group and a physiologically acceptable medium.

A subject of the invention is thus a polymer obtained by reacting said phosphonic polymer with an amine compound as defined previously, the reaction taking place in anhydrous medium when the amine compound is an amino alkoxysilane.

According to a first embodiment of the process according to the invention, an extemporaneous mixture of a composition comprising the phosphonic polymer and of an amine compound as described previously or of a composition containing same and comprising a physiologically acceptable medium is applied to keratin materials.

According to a second embodiment of the process according to the invention, the composition comprising the phosphonic polymer is first applied to the keratin materials, and an amine compound as described previously or a composition containing same and comprising a physiologically acceptable medium is then applied.

According to a third embodiment of the process according to the invention, the amine compound as described previously, or a composition containing the same and comprising a physiologically acceptable medium is first applied to keratin materials, and the cosmetic composition comprising the phosphonic polymer is then applied.

Other particular additional components may be used in the process according to the invention to contribute toward the film-forming properties of the polymer according to the invention. Such additional components are especially the salts of divalent or trivalent metal ions, clays and metal oxides described below.

The composition according to the invention may comprise salts of divalent or trivalent metal ions, chosen in particular from salts of ions derived from Al(III), Ca(II), Cu(II), Fe(II), Fe(III), Mg(II), Mn(II), Zn(II), and mixtures thereof. Ions derived from Ca(II), Mg(II) are preferred.

The salts of these metal ions are well known, with, for example, anions such as gluconate, chloride, sulfate, hydroxide, acetate and stearate. For example, use may be made of the following salts: calcium gluconate, calcium chloride, magnesium chloride, copper chloride, magnesium gluconate, iron sulfate, iron gluconate, aluminium sulfate, sodium stearate; calcium stearate or zinc acetate is preferably used, and preferentially zinc acetate.

Said salts of divalent or trivalent metal ions may be present in the composition according to the invention in a content ranging from 0.1% to 20% by weight, preferably from 0.1% to 15% by weight, relative to the total weight of the composition.

Alternatively, the salt of divalent or trivalent metal ions may be applied sequentially in the process according to the invention.

The composition according to the invention may comprise a clay.

Clays are products that are already well known per se, which are described, for example, in the publication Minéralogie des argiles [Mineralogy of Clays], S. Caillère, S. Hénin, M. Rautureau, 2nd Edition 1982, Masson, the teaching of which is included herein by way of reference.

Among the clays, examples that may be mentioned include clays of the smectite family, such as laponite and montmorillonite, of the kaolinite family, such as kaolinite, dickite, nacrite, optionally modified clays of the halloysite, dombassite, antigorite, benthierine, pyrophyllite, montmorillonite, beidellite, vermiculite, talc, stevensite, hectorite, bentonite, saponite, chlorite, sepiolite and illite family.

The clay(s) present in the composition of the invention may be natural or synthetic. Natural clay is a sedimentary rock composed to a large extent of specific minerals, silicates generally of aluminium. Kaolin is thus a natural clay.

The clays may also be chemically modified by various compounds, such as acrylic acids, polysaccharides (for example carboxymethylcellulose) or organic cations.

Preferably, in the context of the present invention, use is made of clays that are cosmetically compatible with and acceptable for human keratin materials.

According to a particular embodiment of the present invention, the clay used is chosen from kaolinite, montmorillonites, saponites, laponites, bentonites, and in particular hectorites, and illites. Use is even more particularly made of mixtures of clays, and natural clays.

Natural clays that may be mentioned include green clays, in particular rich in illite; clays rich in montmorillonite, known as fuller's earth, or such as bentonite or else white clays rich in kaolinite. Bentonites that may be mentioned in particular include those sold under the names Bentone 38 VCG, Bentone Gel CAO V, Bentone 27 V, Bentone Gel MIO V and Bentone Gel ISD V by the company Elementis.

Montmorillonites and smectites are hydrated aluminium and/or magnesium silicates. Examples that may be mentioned include the montmorillonite sold under the name Gel White H by the company Rockwood Additives, and the purified smectites sold under the name Veegum Granules by the company Vanderbilt. Mention may also be made of the montmorillonite sold under the name Kunipia G4 by the company Kunimine and the sepiolite Pangel S9 sold by the company Tolsa.

Examples of kaolinites that may be mentioned include the kaolins sold under the name Coslin C 100 by the company BASF Personal Care Ingredients or Kaolin Supreme by the company Imerys.

Talcs are hydrated magnesium silicates usually comprising aluminium silicate. The crystal structure of talc consists of repeated layers of a sandwich of brucite between layers of silica. Examples that may be mentioned include micronized magnesium silicate of particle size 5 microns sold under the name Micro Ace P3 by the company Nippon Talc or the talcs sold under the names Rose Talc and Talc SG-2000 by the company Nippon Talc, J 68 BC by the company US Cosmetics (Miyoshi), Lyzenac 00 and Luzenac Pharma M by the company Luzenac, and Talc JA-46R by the company Asada Milling.

As saponite, which belongs to the montmorillonite family, mention may be made of synthetic saponite, in particular the product sold by the company Kunimine under the name Sumecton®.

An example of a synthetic laponite that may be mentioned is the laponite XLG sold by the company Rockwood.

The clay may be present in the composition according to the invention in an amount ranging from 0.1% to 50% by weight, especially from 1% to 30% by weight and in particular from 1% to 20% by weight relative to the total weight of the composition.

The metal oxides may be chosen from titanium dioxide, iron oxides, zirconium oxides, zinc oxides, cerium oxides and chromium oxides. Iron oxides or titanium dioxide are preferably used.

The metal oxide may be present in the composition according to the invention in an amount ranging from 0.1% to 50% by weight, especially from 1% to 30% by weight and in particular from 1% to 20% by weight relative to the total weight of the composition.

Advantageously, the process according to the invention is performed under ambient conditions, in particular at an ambient temperature that may range from 15° C. to 30° C., preferably ranging from 18° C. to 25° C.

The composition used according to the invention is generally suitable for topical application to keratin materials, and thus generally comprises a physiologically acceptable medium, i.e. a medium that is compatible with the keratin materials such as the skin and/or its integuments. It is preferably a cosmetically acceptable medium, i.e. a medium which has a pleasant colour, odour and feel and which does not cause any unacceptable discomfort (stinging, tautness or redness) liable to discourage the consumer from using this composition.

According to a preferred embodiment of the invention, the composition comprising the phosphonic polymer may contain a hydrocarbon-based oil.

The hydrocarbon-based oil is an oil that is liquid at room temperature (25° C.).

The term "hydrocarbon-based oil" means an oil formed essentially from, or even consisting of, carbon and hydrogen atoms, and optionally oxygen and nitrogen atoms, and not containing any silicon or fluorine atoms. It may contain alcohol, ester, ether, carboxylic acid, amine and/or amide groups.

The hydrocarbon-based oil may be volatile or non-volatile.

The hydrocarbon-based oil may be chosen from:
hydrocarbon-based oils containing from 8 to 14 carbon atoms, and especially:
  branched $C_8$-$C_{14}$ alkanes, for instance $C_8$-$C_{14}$ isoalkanes of petroleum origin (also known as isoparaffins), for instance isododecane (also known as 2,2,4,4,6-pentamethylheptane), isodecane and, for example, the oils sold under the trade name Isopar or Permethyl,
  linear alkanes, for instance n-dodecane (C12) and n-tetradecane (C14) sold by Sasol under the respective references Parafol 12-97 and Parafol 14-97, and also mixtures thereof, the undecane-tridecane mixture, the mixtures of n-undecane (C11) and of n-tridecane (C13) obtained in Examples 1 and 2 of patent application WO 2008/155 059 from the company Cognis, and mixtures thereof,
  short-chain esters (containing from 3 to 8 carbon atoms in total) such as ethyl acetate, methyl acetate, propyl acetate or n-butyl acetate,
  hydrocarbon-based oils of plant origin such as triglycerides consisting of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, for instance those sold by the company Stéarineries Dubois or those sold under the names Miglyol 810®, 812° and 818° by the company Dynamit Nobel,
  synthetic ethers having from 10 to 40 carbon atoms;
  linear or branched hydrocarbons of mineral or synthetic origin, such as petroleum jelly, polydecenes, hydrogenated polyisobutene such as Parleam®, squalane and liquid paraffins, and mixtures thereof,
  synthetic esters such as oils of formula $R_1COOR_2$ in which $R_1$ represents a linear or branched fatty acid residue containing from 1 to 40 carbon atoms and $R_2$ represents an, in particular, branched hydrocarbon-based chain containing from 1 to 40 carbon atoms, on the condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters,
  fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol.

Advantageously, the hydrocarbon-based oil is apolar (thus formed solely from carbon and hydrogen atoms).

The hydrocarbon-based oil is preferably chosen from hydrocarbon-based oils containing from 8 to 14 carbon atoms, in particular the apolar oils described previously.

Preferentially, the hydrocarbon-based oil is isododecane.

The composition comprising the polymer may contain, in addition to the hydrocarbon-based oil, a silicone oil. The term "silicone oil" means an oil comprising at least one silicon atom and especially at least one Si—O group. The silicone oil may be volatile or non-volatile.

The term "volatile oil" means an oil (or non-aqueous medium) that is capable of evaporating on contact with the skin in less than one hour, at room temperature and at atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1,300 Pa (0.01 to 10 mmHg).

The term "non-volatile oil" means an oil with a vapour pressure of less than 0.13 Pa.

Volatile silicone oils that may be mentioned include volatile linear or cyclic silicone oils, especially those with a viscosity ≤8 centistokes (cSt) ($8 \times 10^{-6}$ m$^2$/s), and especially having from 2 to 10 silicon atoms and in particular from 2 to 7 silicon atoms, these silicones optionally comprising alkyl or alkoxy groups having from 1 to 10 carbon atoms.

As volatile silicone oils that may be used in the invention, mention may be made especially of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As non-volatile silicone oils, mention may be made of linear or cyclic non-volatile polydimethylsiloxanes (PDMSs); polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

Advantageously, the composition may comprise a hydrocarbon-based oil in a content ranging from 60% to 100% by weight relative to the total weight of the oils present in the composition and from 0 to 40% by weight of silicone oil. According to a preferred embodiment of the invention, the composition contains as oil only a hydrocarbon-based oil.

The composition according to the invention may comprise a cosmetic additive chosen from fragrances, preserving agents, fillers, UV-screening agents, oils, waxes, surfactants, moisturizers, vitamins, ceramides, antioxidants, free-radical scavengers, polymers, thickeners and dyestuffs.

The composition according to the invention may also comprise a dyestuff such as pulverulent dyestuffs, liposoluble dyes or water-soluble dyes. This dyestuff may be present in a content ranging from 0.01% to 30% by weight, relative to the total weight of the composition.

The pulverulent dyestuffs may be chosen from pigments and nacres.

The pigments may be white or coloured, mineral and/or organic, and coated or uncoated. Among the mineral pigments that may be mentioned are titanium dioxide, optionally surface-treated, zirconium, zinc or cerium oxide, and also iron or chromium oxide, manganese violet, ultramarine blue, chromium hydrate and ferric blue. Among the organic pigments that may be mentioned are carbon black, pigments of D & C type and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica with in particular ferric blue or chromium oxide, titanium mica with an organic pigment of the abovementioned type, and also nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto. The water-soluble dyes are, for example, beetroot juice or methylene blue.

Advantageously, the composition according to the invention is a skincare composition.

The composition according to the invention may be a makeup composition such as a foundation, a lipstick or a liner.

According to one embodiment, the composition according to the invention is a makeup composition and comprises a volatile oil and a nonvolatile oil as described previously. In particular, the makeup composition may comprise a hydrocarbon-based volatile oil and a hydrocarbon-based nonvolatile oil.

According to one embodiment, the composition according to the invention is an anhydrous composition. The term "anhydrous composition" means a composition containing less than 2% by weight of water, or even less than 0.5% of water, and is especially free of water. Where appropriate, such small amounts of water may especially be introduced by ingredients of the composition that may contain residual amounts thereof.

In particular, when the amine compound is an amino alkoxysilane (III) as defined previously, the composition containing it and the compositions used in the process are anhydrous compositions. Advantageously, these compositions also contain a $C_2$-$C_5$ monoalcohol such as ethanol or isopropanol, especially in a content ranging from 0.1% to 5% by weight, relative to the total weight of the composition.

The invention will now be described with reference to the examples that follow, which are given as non-limiting illustrations.

EXAMPLE 1

2-Ethylhexyl Acrylate/Vinylphosphonic Acid Copolymer (90/10 Mass Composition) Polymer 1

180 g of 2-ethylhexyl acrylate and 20 g of vinylphosphonic acid were placed in a jacketed 1-litre reactor equipped with a stirring anchor, followed by addition of 300 g of isododecane. The system was sparged with argon for 10 minutes, and 3 g of initiator tert-butyl peroxy-2-ethylhexanoate (Trigonox® 21S from AkzoNobel) were then added. The heating of the jacket was set at 90° C. for 7 hours at 150 rpm.

The medium was then diluted with 300 g of isododecane, and then concentrated by distillation to remove the unreacted monomers. A solution containing 50% by weight of the polymer in isododecane was finally obtained.

The polymer obtained has a number-average molecular weight (Mn) of 6800 and a weight-average molecular weight (Mw) of 138 000.

EXAMPLE 2

2-Ethylhexyl Acrylate/Isobornyl Acrylate/Vinylphosphonic Acid Copolymer (70/20/10 Mass Composition) Polymer 2

The polymer was prepared according to the procedure of Example 1, using 140 g of 2-ethylhexyl acrylate, 40 g of isobornyl acrylate and 20 g of vinylphosphonic acid. A solution containing 50% by weight of the polymer in isododecane was finally obtained.

The polymer obtained has a number-average molecular weight (Mn) of 4800 and a weight-average molecular weight (Mw) of 10 000.

EXAMPLES 3 AND 4

Cosmetic Evaluation of Makeup Compositions with Application in One Step

The makeup compositions (lip gloss) described below containing the polymer of Example 1 with or without 3-aminopropyl-terminated polydimethylsiloxane were prepared, and the composition was then applied onto a skin equivalent support made of elastomer by producing a deposit with a wet thickness of 100 µm, which was left to dry at room temperature (25° C.) for 24 hours.

The state of the film obtained was then observed.

The elastomer support was also deformed manually and the state of the film after this deformation was observed to determine its resistance to deformation.

The resistance of the film obtained was evaluated by separately applying 0.5 ml of water, 0.5 ml of olive oil and 0.5 ml of sebum; after 5 minutes of contact, the surface of the film was rubbed with cotton wool and the state of the film was then observed (degraded or undegraded appearance of the film).

The tackiness of the film and its capacity for transferring or not transferring on touching the film with a finger were also evaluated.

The evaluation was made in the following manner:

+++: very efficient evaluated cosmetic property
++: moderately efficient evaluated cosmetic property
+: sparingly efficient evaluated cosmetic property
0: inefficient evaluated cosmetic property The following results were obtained:

| Composition | Example 3 | Example 4 |
|---|---|---|
| Polymer of Example 1 | 25 g AM | 25 g AM |
| Pigmentary paste containing 40% by weight of pigment in isododecane | 5 g with DC Red 7 | 5 g with DC Red 7 |
| 3-Aminopropyl-terminated polydimethylsiloxane | — | 2.5 g |
| (Mn 2500; reference 481688 from Sigma) | | |
| Isododecane | 70 g | 67.5 g |

| Evaluation of the film | Example 3 | Example 4 |
|---|---|---|
| Appearance of the film | Homogeneous film | Homogeneous film |
| Resistance to deformation | Yes without damaging the film | Yes without damaging the film |
| Water resistance | ++ | +++ |
| Olive oil resistance | 0 | + |
| Sebum resistance | 0 | + |
| Non-tacky | 0 | + |
| Transfer-resistant | 0 | + |

The results obtained show that the deposit resulting from the application of polymer 1 alone (Example 3) forms a homogeneous film, which is not fragmented after mechanical stress, but the film is tacky, transfers onto the finger and is not resistant to contact with olive oil and sebum.

The deposit resulting from the application of polymer 1 mixed with the 3-aminopropyl-terminated polydimethylsiloxane (Example 4) forms a homogeneous film, which is not fragmented after mechanical stress, and shows an improvement in the non-tacky and transfer-resistance properties and in the resistance of the film to contact with olive oil and sebum, compared with the film of Example 3.

Thus, the addition of the 3-aminopropyl-terminated polydimethylsiloxane contributes toward improving the cosmetic properties of the film obtained.

The lipstick composition of Example 4 applied to the lips thus makes it possible to obtain a non-tacky, transfer-resistant and water-, oil- and sebum-resistant makeup which thus has good persistence.

EXAMPLES 5 AND 6

Cosmetic Evaluation of Makeup Compositions with Application in One Step

The makeup compositions (lip gloss) described below containing the polymer of Example 2 with or without disteardimonium hectorite were prepared, and the cosmetic properties were then evaluated according to the protocols described in the preceding Examples 3 and 4.

The following results were obtained:

| Composition | Example 5 | Example 6 |
|---|---|---|
| Polymer of Example 2 | 25 g AM | 25 g AM |
| Pigmentary paste containing 40% by weight of pigment in isododecane | 5 g with DC Red 7 | 5 g with DC Red 7 |
| Disteardimonium hectorite | — | 10 g |

|  | Example 5 | Example 6 |
|---|---|---|
| (Bentone Gel ISD V from Elementis) Isododecane | 70 g | 60 g |
| Evaluation of the film |  |  |
| Appearance of the film | Homogeneous film | Homogeneous film |
| Resistance to deformation | Yes without damaging the film | Yes without damaging the film |
| Water resistance | ++ | +++ |
| Olive oil resistance | 0 | ++ |
| Sebum resistance | 0 | ++ |
| Non-tacky | 0 | ++ |
| Transfer-resistant | 0 | ++ |

The results obtained show that the deposit resulting from the application of polymer 2 alone (Example 5) forms a homogeneous film, which is not fragmented after mechanical stress, but the film is tacky, transfers onto the finger and is not resistant to contact with olive oil and sebum.

The deposit resulting from the application of polymer 2 mixed with disteardimonium hectorite (Example 6) forms a homogeneous film, which is not fragmented after mechanical stress, and shows good improvement in the non-tacky and transfer-resistance properties and in the resistance of the film to contact with water, olive oil and sebum, compared with the film of Example 5.

Thus, the addition of disteardimonium hectorite contributes toward improving the cosmetic properties of the film obtained.

The lipstick composition of Example 6 applied to the lips thus makes it possible to obtain a non-tacky, transfer-resistant and water-, oil- and sebum-resistant makeup which thus has good persistence.

EXAMPLE 7

Cosmetic Evaluation of Makeup Compositions with Application in One Step

The makeup compositions (lip gloss) described below containing the polymer of Example 2 with or without 3-aminopropyl-terminated polydimethylsiloxane were prepared, and the cosmetic properties were then evaluated according to the protocols described in the preceding Examples 3 and 4.

The following results were obtained:

|  | Example 5 | Example 7 |
|---|---|---|
| Composition |  |  |
| Polymer of Example 2 | 25 g AM | 25 g AM |
| Pigmentary paste containing 40% by weight of pigment in isododecane | 5 g with DC Red 7 | 5 g with DC Red 7 |
| 3-Aminopropyl-terminated polydimethylsiloxane (Mn 2500; reference 481688 from Sigma) | — | 2.5 g |
| Isododecane | 70 g | 67.5 g |
| Evaluation of the film |  |  |
| Appearance of the film | Homogeneous film | Homogeneous film |
| Resistance to deformation | Yes without damaging the film | Yes without damaging the film |
| Water resistance | ++ | +++ |
| Olive oil resistance | 0 | +++ |
| Sebum resistance | 0 | +++ |
| Non-tacky | 0 | ++ |
| Transfer-resistant | 0 | +++ |

The deposit resulting from the application of polymer 2 mixed with 3-aminopropyl-terminated polydimethylsiloxane (Example 7) forms a homogeneous film, which is not fragmented after mechanical stress, and shows good improvement in the non-tacky and transfer-resistance properties and in the resistance of the film to contact with water, olive oil and sebum, compared with the film of Example 5.

Thus, the addition of the 3-aminopropyl-terminated polydimethylsiloxane contributes toward improving the cosmetic properties of the film obtained.

The lipstick composition of Example 7 applied to the lips thus makes it possible to obtain a non-tacky, transfer-resistant and water-, oil- and sebum-resistant makeup which thus has good persistence.

EXAMPLES 8 AND 9

Cosmetic Evaluation of Makeup Compositions with Application in One Step

The makeup compositions described below containing the polymer of Example 2 with or without 3-aminopropyl-terminated polydimethylsiloxane and containing 2-octyldodecanol (nonvolatile oil) were prepared, and the cosmetic properties were then evaluated according to the protocols described in the preceding Examples 3 and 4.

The following results were obtained:

|  | Example 8 | Example 9 |
|---|---|---|
| Composition |  |  |
| Polymer of Example 2 | 25 g AM | 25 g AM |
| Pigmentary paste containing 40% by weight of pigment in isododecane | 5 g with DC Red 7 | 5 g with DC Red 7 |
| 3-Aminopropyl-terminated polydimethylsiloxane (Mn 2500; reference 481688 from Sigma) | — | 2.5 g |
| 2-Octyldodecanol | 20 g | 20 g |
| Isododecane | 50 g | 37.5 g |
| Evaluation of the film |  |  |
| Appearance of the film | Homogeneous film | Homogeneous film |
| Resistance to deformation | Yes without damaging the film | Yes without damaging the film |

-continued

|  | Example 8 | Example 9 |
|---|---|---|
| Water resistance | ++ | +++ |
| Olive oil resistance | 0 | + |
| Sebum resistance | 0 | + |
| Non-tacky | 0 | + |
| Transfer-resistant | 0 | + |

The results obtained show that the deposit resulting from the application of polymer 2 alone and of 2-octyldodecanol (Example 8) forms a homogeneous film, which is not fragmented after mechanical stress, but the film is tacky, transfers onto the finger and is not resistant to contact with olive oil and sebum.

The deposit resulting from the application of polymer 1 and 2-octyldodecanol mixed with the 3-aminopropyl-terminated polydimethylsiloxane (Example 9) forms a homogeneous film, which is not fragmented after mechanical stress, and shows an improvement in the non-tacky and transfer-resistance properties and in the resistance of the film to contact with water, olive oil and sebum, compared with the film of Example 8.

Thus, the addition of the 3-aminopropyl-terminated polydimethylsiloxane contributes toward improving the cosmetic properties of the film obtained.

EXAMPLES 10 AND 11

Cosmetic Evaluation of Makeup Compositions with Application in One Step

The makeup compositions described below containing the polymer of Example 2 with or without red iron oxides were prepared, and the cosmetic properties were then evaluated according to the protocols described in the preceding Examples 3 and 4.

The following results were obtained:

|  | Example 10 | Example 11 |
|---|---|---|
| Composition |  |  |
| Polymer of Example 2 | 25 g AM | 25 g AM |
| Pigmentary paste containing 40% by weight of red iron oxide in isododecane | — | 5 g |
| Isododecane | 75 g | 70 g |
| Evaluation of the film |  |  |
| Appearance of the film | Homogeneous film | Homogeneous film |
| Resistance to deformation | Yes without damaging the film | Yes without damaging the film |
| Olive oil resistance | 0 | +++ |
| Sebum resistance | 0 | +++ |
| Non-tacky | 0 | +++ |
| Transfer-resistant | 0 | +++ |

The results obtained show that the deposit resulting from the application of polymer 2 alone (Example 10) forms a homogeneous film, which is not fragmented after mechanical stress, but the film is tacky, transfers onto the finger and is not resistant to contact with olive oil and sebum.

The deposit resulting from the application of polymer 2 mixed with red iron oxide (Example 11) forms a homogeneous film, which is not fragmented after mechanical stress, and shows a large improvement in the non-tacky and transfer-resistance properties and in the resistance of the film to contact with olive oil and sebum, compared with the film of Example 10.

Thus, the addition of red iron oxide contributes toward improving the cosmetic properties of the film obtained.

EXAMPLES 12 AND 13

Cosmetic Evaluation of Makeup Composition with Application in Two Steps

The two base coat makeup compositions (lip gloss) containing the polymer of Example 2 and a top coat composition containing 3-aminopropyl-terminated polydimethylsiloxane described below were prepared.

Each base coat composition was applied onto a skin equivalent support made of elastomer by producing a deposit with a wet thickness of 100 μm, which was left to dry at room temperature (25° C.) for 24 hours.

The top coat composition was then applied onto the dry base coat deposit by producing a deposit with a wet thickness of 100 μm, which was left to dry at room temperature (25° C.) for 24 hours.

The cosmetic properties of the film obtained before (outside the invention) and after (invention) applying the top coat composition were evaluated according to the protocols described in the preceding Examples 3 and 4.

The following results were obtained:

|  | Example 12 | Example 13 |
|---|---|---|
| Base Coat |  |  |
| Polymer of Example 2 | 25 g | 25 g |
| Pigmentary paste containing 40% by weight of pigment in isododecane | 5 g with DC Red 7 | 5 g with DC Red 7 |
| Disteardimonium hectorite (Bentone Gel ISD V from Elementis) | 10 g | 10 g |
| Isododecane | qs 100 g | qs 100 g |
| Top Coat | No | Yes |
| 3-Aminopropyl-terminated polydimethylsiloxane (Mn 2 500; reference 481688 from Sigma) |  | 10 g |
| Isododecane |  | 90 g |
| Appearance of the film | Homogeneous film | Homogeneous film |
| Resistance to deformation | Yes without damaging the film | Yes without damaging the film |
| Water resistance | ++ | +++ |
| Olive oil resistance | 0 | ++ |
| Sebum resistance | 0 | ++ |
| Non-tacky | 0 | ++ |
| Transfer-resistant | 0 | ++ |

The results obtained show that the deposit resulting from the application of polymer 2 followed by the 3-aminopropyl-terminated polydimethylsiloxane (Example 13) forms a non-tacky homogeneous film that does not transfer by finger, and that is resistant to water, to oil and to sebum, whereas the sole application of polymer 2 (Example 12) forms a deposit that is much more tacky and that transfers onto the finger and has poor resistance to water, to oil and to sebum.

Thus, the non-tacky and transfer-resistant aspect on contact with the finger, and also the resistance of the film to contact with water, olive oil and sebum are markedly improved with the application of the top coat composition containing 3-aminopropyl-terminated polydimethylsiloxane.

The lipstick compositions of Example 13 applied to the lips thus make it possible to obtain a non-tacky, transfer-resistant and water-, oil- and sebum-resistant makeup which thus has good persistence.

EXAMPLES 14 AND 15

Cosmetic Evaluation of Makeup Compositions with Application in One Step

The makeup compositions described below containing the polymer of Example 2 with or without 3-aminopropyltriethoxysiloxane (APTES) and with or without 2-octyldodecanol (nonvolatile oil) were prepared, and the cosmetic properties were then evaluated according to the protocols described in the preceding Examples 3 and 4.

The following results were obtained:

|  | Example 5 | Example 14 | Example 15 |
| --- | --- | --- | --- |
| Composition |  |  |  |
| Polymer of Example 2 | 25 g AM | 25 g AM | 25 g AM |
| Pigmentary paste containing 40% by weight of pigment in isododecane | 5 g with DC Red 7 | 5 g with DC Red 7 | 5 g with DC Red 7 |
| APTES | — | 2.5 g | 2.5 g |
| 2-Octyldodecanol | — | — | 20 g |
| Isododecane | 70 g | 67.5 g | 47.5 g |
| Evaluation of the film |  |  |  |
| Appearance of the film | Homogeneous film | Homogeneous film | Homogeneous film |
| Resistance to deformation | Yes without damaging the film | Yes without damaging the film | Yes without damaging the film |
| Water resistance | ++ | +++ | +++ |
| Olive oil resistance | 0 | +++ | ++ |
| Sebum resistance | 0 | +++ | ++ |
| Non-tacky | 0 | ++ | + |
| Transfer-resistant | 0 | +++ | + |

The deposit resulting from the application of polymer 2 mixed with APTES (Examples 14, 15) forms a homogeneous film, which is not fragmented after mechanical stress, and shows good improvement in the non-tacky and transfer-resistance properties and in the resistance of the film to contact with water, olive oil and sebum, compared with the film of Example 5.

Thus, the addition of APTES contributes toward improving the cosmetic properties of the film obtained.

EXAMPLES 16 AND 17

The makeup compositions (lip gloss) described below containing the polymer of Example 2 with or without calcium stearate or zinc acetate were prepared, and the cosmetic properties were then evaluated according to the protocols described in the preceding Examples 3 and 4.

The following results were obtained:

|  | Example 5 | Example 16 | Example 17 |
| --- | --- | --- | --- |
| Composition |  |  |  |
| Polymer of Example 2 | 25 g AM | 25 g AM | 25 g AM |
| Pigmentary paste containing 40% by weight of pigment in isododecane | 5 g with DC Red 7 | 5 g with DC Red 7 | 5 g with DC Red 7 |
| Calcium stearate | — | 3.75 g | — |
| Zinc acetate | — | — | 3.75 g |
| Isododecane | qs 100 g | qs 100 g | qs 100 g |
| Evaluation of the film |  |  |  |
| Appearance of the film | Homogeneous film | Homogeneous film | Homogeneous film |
| Resistance to deformation | Yes without damaging the film | Yes without damaging the film | Yes without damaging the film |
| Olive oil resistance | 0 | ++ | +++ |
| Sebum resistance | 0 | ++ | +++ |
| Non-tacky | 0 | +++ | +++ |
| Transfer-resistant | 0 | ++ | +++ |

The results obtained show that the deposit resulting from the application of polymer 2 alone (Example 5) forms a homogeneous film, which is not fragmented after mechanical stress, but the film is tacky, transfers onto the finger and is not resistant to contact with olive oil and sebum.

The deposits resulting from the application of polymer 2 mixed with calcium stearate (Example 16) or zinc acetate (Example 17) form a homogeneous film, which is not fragmented after mechanical stress, and show good improvement in the non-tacky and transfer-resistance properties and in the resistance of the film to contact with olive oil and sebum, compared with the film of Example 5.

Thus, the addition of calcium stearate or zinc acetate contributes toward improving the cosmetic properties of the film obtained.

The lipstick compositions of Examples 16 and 17 applied to the lips thus make it possible to obtain a non-tacky, transfer-resistant and oil- and sebum-resistant makeup which thus has good persistence.

The invention claimed is:

1. A cosmetic process for treating keratin materials, comprising the topical application to the keratin materials of a composition comprising, in a physiologically acceptable medium, a phosphonic polymer derived from the polymerization of:
   (a) 45% to 95% by weight, relative to the total weight of monomers, of an ethylenic monomer bearing an at least $C_8$ linear or branched alkyl group;
   (b) 5% to 25% by weight of vinylphosphonic acid monomer of formula (I);
   (c) 0% to 50% by weight of additional monomer chosen from:
   (i) linear or branched $C_1$-$C_6$ alkyl (meth)acrylate or $C_6$-$C_{12}$ cycloalkyl (meth)acrylate non-silicone monomers;
   (ii) polydimethylsiloxane silicone monomers bearing a mono(meth)acryloyloxy end group of formula (II) below:

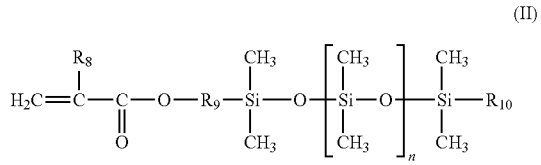

in which:
R$_8$ denotes a hydrogen atom or a methyl group;
R$_9$ denotes a linear or branched divalent hydrocarbon-based group containing from 1 to 10 carbon atoms and optionally containing one or two ether bonds —O—;
R$_{10}$ denotes a linear or branched alkyl group containing from 1 to 10 carbon atoms;
n denotes an integer ranging from 1 to 300;
said vinylphosphonic acid monomer of formula (I) being:

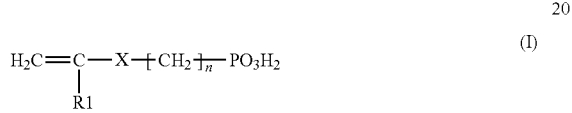

in which:
R1 denotes H or —CH$_3$;
X denotes a covalent bond and n denotes an integer ranging from 0 to 14;
or X denotes a —COO— group and n denotes an integer ranging from 2 to 6.

2. The process according to claim 1, wherein the ethylenic monomer bearing an at least C$_8$ linear or branched alkyl group is chosen from:
a) linear or branched C$_8$-C$_{22}$ alkyl (meth)acrylates;
b) the (meth)acrylamides of formula CH$_2$=C(R$_1$)—CONR$_3$R$_4$ in which R$_1$ represents a hydrogen atom or a methyl radical, R$_3$ represents a hydrogen atom or a linear or branched C$_1$-C$_{12}$ alkyl group, and R$_4$ represents a linear or branched C$_8$ to C$_{12}$ alkyl group;
c) the vinyl esters of formula R$_5$—CO—O—CH=CH$_2$ in which R$_5$ represents a linear or branched C$_8$-C$_{22}$ alkyl group;
d) the ethers of formula R$_6$—O—CH=CH$_2$ in which R$_6$ represents a linear or branched C$_8$-C$_{22}$ alkyl group.

3. The process according to claim 1, wherein the ethylenic monomer bearing an at least C$_8$ linear or branched alkyl group is chosen from linear or branched C$_8$-C$_{22}$ alkyl (meth)acrylates.

4. The process according to claim 1, wherein ethylenic monomer bearing an at least C$_8$ linear or branched alkyl group is chosen from 2-ethylhexyl acrylate, 2-ethylhexyl methacrylate, lauryl acrylate, lauryl methacrylate, behenyl acrylate, behenyl methacrylate, stearyl acrylate, and stearyl methacrylate.

5. The process according to claim 1, wherein the ethylenic monomer bearing an at least C$_8$ linear or branched alkyl group is present in said phosphonic polymer in a content ranging from 55% to 95% by weight, relative to the total weight of monomers.

6. The process according to claim 1, wherein, for the monomer (I), X denotes a covalent bond and n is an integer ranging from 0 to 6 or X denotes a —COO— group and n is an integer ranging from 2 to 4.

7. The process according to claim 1, wherein for monomer (I), R1=H and X denotes a covalent bond and n is an integer ranging from 0 to 4.

8. The process according to claim 1, wherein monomer (I) is chosen from:
vinylphosphonic acid;
3-butenylphosphonic acid;
4-pentenylphosphonic acid;
10-undecenylphosphonic acid;
11-dodecenylphosphonic acid;
2-phosphonoethyl ester of 2-methyl-2-propenoic acid; and
2-phosphonoethyl ester of 2-propenoic acid.

9. The process according to claim 1, wherein said additional monomer is non-silicone and is chosen from C$_6$-C$_{12}$ cycloalkyl (meth)acrylates.

10. The process according to claim 1, wherein for said silicone monomer of formula (II):
R$_8$ denotes a methyl group;
R$_9$ denotes a linear divalent hydrocarbon-based group containing from 2 to 4 carbon atoms;
R$_{10}$ denotes a linear or branched alkyl group, comprising from 2 to 8 carbon atoms;
n denotes an integer ranging from 3 to 200.

11. The process according to claim 1, wherein said phosphonic polymer comprises the additional monomer present in a content ranging from 5% to 50% by weight, relative to the total weight of monomers.

12. The process according to claim 1, wherein said phosphonic polymer does not contain any additional monomer (c).

13. The process according to claim 1, wherein said phosphonic polymer comprises, or consists of:
(a) 75% to 95% by weight, relative to the total weight of monomers, of linear or branched C$_8$-C$_{22}$ alkyl (meth)acrylate; and
(b) 5% to 25% by weight of vinylphosphonic acid monomer (I).

14. The process according to claim 1, wherein said phosphonic polymer is chosen from the following copolymers:
2-ethylhexyl acrylate/vinylphosphonic acid
stearyl acrylate/vinylphosphonic acid
2-ethylhexyl acrylate/stearyl acrylate/vinylphosphonic acid.

15. The process according to claim 1, wherein said phosphonic polymer comprises, or consists of:
(a) 45% to 94.5% by weight, relative to the total weight of monomers, of linear or branched C$_8$-C$_{18}$ alkyl (meth)acrylate;
(b) 5% to 25% by weight of vinylphosphonic acid monomer (I);
(c) 0.5% to 50% by weight of C$_6$-C$_{12}$ cycloalkyl (meth)acrylate.

16. The process according to claim 1, wherein the phosphonic polymer is chosen from the following copolymers:
2-ethylhexyl acrylate/vinylphosphonic acid/isobornyl (meth)acrylate
stearyl acrylate/vinylphosphonic acid/isobornyl (meth)acrylate
2-ethylhexyl acrylate/stearyl acrylate/vinylphosphonic acid/isobornyl (meth)acrylate.

17. The process according to claim 1, wherein the phosphonic polymer comprises, or consists of:
(a) 45% to 94.5% by weight, relative to the total weight of monomers, of linear or branched C$_8$-C$_{22}$ alkyl (meth)acrylate;
(b) 5% to 25% by weight of vinylphosphonic acid monomer (I);
(c) 0.5% to 50% by weight of silicone monomer (II).

18. The process according to claim 1, wherein the phosphonic polymer is chosen from the following copolymers:
2-ethylhexyl acrylate/vinylphosphonic acid/silicone monomer (II)
stearyl acrylate/vinylphosphonic acid/silicone monomer (II)
2-ethylhexyl acrylate/stearyl acrylate/vinylphosphonic acid/silicone monomer (II).

19. The process according to claim 1, wherein the phosphonic polymer has a weight-average molecular weight ranging from 5000 to 1 000 000 g/mol.

20. The process according to claim 1, wherein:
either a composition derived from the mixing of a composition comprising the phosphonic polymer and of an additional component, or a composition containing same and comprising a physiologically acceptable medium, is applied topically to keratin materials, the composition derived from the mixing being anhydrous when the additional component is an amino alkoxysilane;
or a composition comprising the phosphonic polymer and an additional component or a composition containing same and comprising a physiologically acceptable medium are applied sequentially to keratin materials, the additional component being chosen from:
(i) an amine compound chosen from polyamine compounds bearing several primary amine and/or secondary amine groups and amino alkoxysilanes,
(ii) salts of divalent or trivalent metal ions,
(iii) clays,
(iv) metal oxides,
the compositions used being anhydrous when the additional component is an amino alkoxysilane.

21. The process according to claim 20, wherein the polyamine compound comprises from 2 to 20 carbon atoms.

22. The process according to claim 20, wherein the polyamine compound is chosen from N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine, 1,3-propylenedimaine, 1,4-butylenediamine, lysine, cystamine, xylenediamine, tris(2-aminoethyl)amine and spermidine.

23. The process according to claim 20, wherein the amino alkoxysilane is of formula (III):

in which:
R'$_1$ is a linear or branched, saturated or unsaturated, cyclic or acyclic $C_1$-$C_6$ hydrocarbon-based chain substituted with a group chosen from the following groups:
amine $NH_2$ or NHR with R=$C_1$-$C_4$ alkyl,
an aryl or aryloxy group substituted with an amino group or with a $C_1$-$C_4$ aminoalkyl group,
R'$_1$ possibly being interrupted in its chain with a heteroatom (O, S, NH) or a carbonyl group (CO), R'$_1$ being linked to the silicon atom directly via a carbon atom,
R'$_2$ and R'$_3$, which may be identical or different, represent a linear or branched alkyl group comprising from 1 to 6 carbon atoms,
z denotes an integer ranging from 1 to 3, and
x denotes an integer ranging from 0 to 2,
with z+x=3.

24. The process according to claim 20, wherein the polyamine compound is chosen from amine-based polymers.

25. The process according to claim 24, wherein the polyamine compound is an amine-based polymer chosen from poly(($C_2$-$C_5$)alkyleneimines; poly(allylamine); polyvinylamines and copolymers thereof; vinylamine/vinylformamide copolymers; polyamino acids bearing $NH_2$ groups; amino polyvinyl alcohol, acrylamidopropylamine-based copolymers; chitosans;
polydimethylsiloxanes comprising primary amine groups at the chain end or on side chains;
amodimethicones of formula (D):

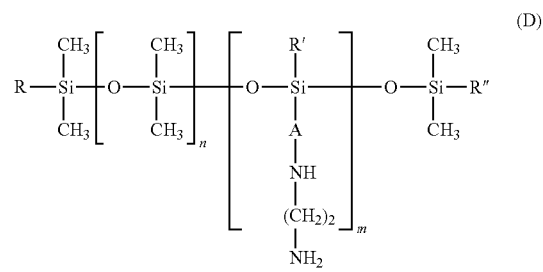

in which R, R' and R'', which may be identical or different, each represent a $C_1$-$C_4$ alkyl or hydroxyl group, A represents a $C_3$ alkylene group and m and n are such that the weight-average molecular mass of the compound is between 5000 and 500 000 approximately;
amodimethicones of formula (K):

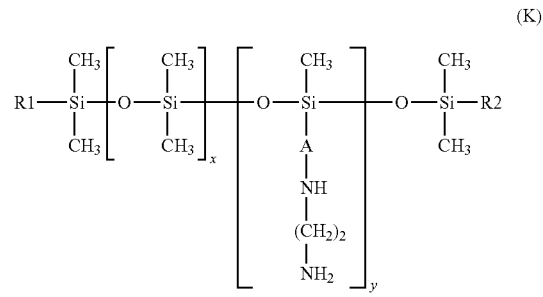

in which:
R1 and R2, which may be identical or different, represent a linear or branched, saturated or unsaturated alkyl group comprising from 6 to 30 carbon atoms,
A represents a linear or branched alkylene group containing from 2 to 8 carbon atoms,
x and y are integers ranging from 1 to 5000;
polyetherdiamines; polytetrahydrofuran (or polytetramethylene glycol) α,ω-diamines and polybutadiene α,ω-diamines;
polyamidoamine dendrimers bearing amine end functions; and
poly(meth)acrylates or poly(meth)acrylamides bearing primary or secondary amine side functions.

26. The process according to claim 20, wherein the additional component is an amine compound chosen from polydimethylsiloxanes comprising primary amine groups at the chain end or on side chains and 3-aminopropyltriethoxysilane.

27. The process according to claim 20, wherein the amine compound is used in a mole ratio of amine group of the amine compound/phosphonic acid of the polymer ranging from 0.01 to 10.

28. The process according to claim 20, wherein when the composition used contains an amino alkoxysilane, it comprises a $C_2$-$C_5$ monoalcohol.

29. The process according to claim 20, wherein the additional component is a clay chosen from clays of the smectite family, of the kaolinite family, optionally modified clays of the halloysite, dombassite, antigorite, benthierine, pyrophyllite, montmorillonite, beidellite, vermiculite, talc, stevensite, hectorite, bentonite, saponite, chlorite, sepiolite and illite family.

30. The process according to claim 20, wherein the additional component is a salt of divalent or trivalent metal ions chosen from salts of ions derived from Al(III), Ca(II), Cu(II), Fe(II), Fe(III), Mg(II), Mn(II), Zn(II) and mixtures thereof.

31. The process according to claim 20, wherein the additional component is a metal oxide chosen from titanium dioxide, iron oxides, zirconium oxides, zinc oxides, cerium oxides and chromium oxides.

32. The process according to claim 20, wherein the mixing of the composition comprising the phosphonic polymer and the additional component, or of the composition containing same, is performed in a time of between 1 minute and 24 hours before its application to keratin materials.

33. The process according to claim 1, wherein the composition applied to the keratin materials comprises a hydrocarbon-based oil.

* * * * *